United States Patent [19]

Tagaya

[11] Patent Number: 4,664,525
[45] Date of Patent: May 12, 1987

[54] METHOD AND APPARATUS FOR DETECTING INFERIOR CONTAINER

[75] Inventor: Ryosaku Tagaya, Isesaki, Japan

[73] Assignee: Eisai Co., Ltd., Tokyo, Japan

[21] Appl. No.: 712,604

[22] Filed: Mar. 18, 1985

[30] Foreign Application Priority Data

Mar. 30, 1984 [JP] Japan ................................ 59-62663

[51] Int. Cl.⁴ .......................................... G01N 21/90
[52] U.S. Cl. ................... 356/428; 209/526; 250/223 B
[58] Field of Search .................... 356/428; 250/223 B; 209/526

[56] References Cited

U.S. PATENT DOCUMENTS 3,439,178  4/1969  Rottmann ........................ 250/223 B
4,280,624  7/1981  Ford ................................. 250/223 B
4,500,203  2/1985  Bieringer ......................... 250/223 B

FOREIGN PATENT DOCUMENTS 73786  6/1977  Japan ............................... 250/223 B Primary Examiner—R. A. Rosenberger
Attorney, Agent, or Firm—Murray and Whisenhunt

[57] ABSTRACT

In a method for detecting an inferior container, wherein: light beams are projected in different two directions upon a side of a transparent or a semitransparent test container while the container is rotatably driven; both of a transmitted beam which is one of the above light beams, having penetrated through the container, and a refelected beam which is the other of the above light beams, having reflected from the container are simultaneously received by a common photo-receptive surface; a composite image constructed of both of the transmitted beam and the reflected beam is projected upon this photo-receptive surface; and an inferior container is detected by means of a shadow formed in this image.

8 Claims, 12 Drawing Figures

FIG. 7
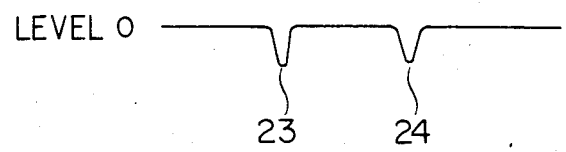
FIG. 8 　　　　FIG. 10
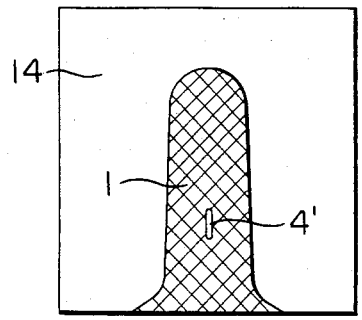 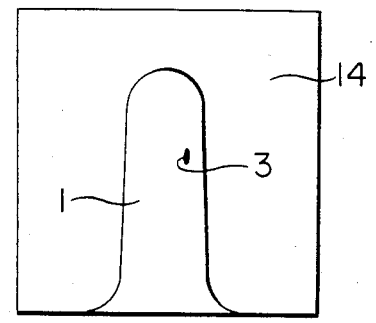
FIG. 9
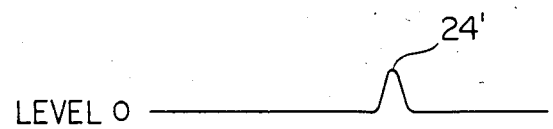
FIG. 11
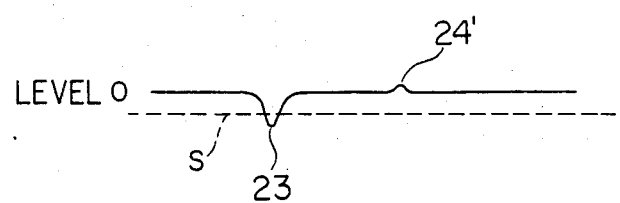

METHOD AND APPARATUS FOR DETECTING INFERIOR CONTAINER

BACKGROUND OF THE INVENTION

1. Field of the Invention

The present invention relates to a method and apparatus for detecting an inferior container which is transparent or semitransparent.

2. Description of the Prior Art:

As a kind of the container, there is a sealed ampoule, which will be hereinafter described.

FIG. 1A shows an ampoule A in manufacturing of which: an ampoule blank "a" having an opening 2 at its top portion of a head 1 thereof as shown in FIG. 1B is filled with a solution or a solid substance fed thereto through the opening 2; and then the opening 2 is heated and melted to be sealed.

In the above case, in filling operation of the solutiion, there occurs many problems in which: the solution fed from a filling nozzle (not shown) is scattered; a front tip of the filling nozzle touches an inner wall of the head 1; or the blank "a" is splashed up to an upper inner wall of its head 1 with the filled solution due to a gas pressure produced in gas exchanging just before the ampoule is sealed in melted manner, which splash adhered to the inner wall of the head 1 is carbonized by heat applied thereto at a time of a melting/sealing operation of the blank "a" to become a scorch stuck to the inner wall. In addition to the above problems, there occur some other problems in which: a stain adheres to the inner wall of the blank "a"; a foreign matter is mixed into the solution; and so on. Consequently, a container having the above problems should be removed as an inferior one.

Hitherto, in detecting of such inferior container, a white board is placed behind the ampoule A which is subjected to an overhead lighting while the ampoule A is visually inspected by an operator. Therefore, such conventional detecting method has defects in that a detecting accuracy thereof varies widely due to differences in experience and sensitivity of the operator while the detecting accuracy itself is poor and an eye strain is caused in the operator. Further, the conventional detecting method has another defect in that an efficiency thereof is poor.

Consequently, the inventor of the present invention previously intended to eliminate such defects. For this purpose, it was proposed that a light source was disposed in a side of the ampoule throuth a light diffusion plate interposed therebetween, and a light beam from the light source through the diffusion plate was projected upon the side surface of the ampoule, of which light beam a light beam penetrated through the ampoule was received by a photo sensor to detect shadows produced by the scorch and the stain, which shadows are converted into an electric signal which is issued to a processing circuit so as to make it possible to detect the inferior container.

However, in such a conventional detecting apparatus, a shadow 4 produced by a flaw, bubble and the like (hereinafter referred to as the flaw and the like) all of which are produced in manufacturing process of the ampoule and are harmless in use is detected by the photo sensor 14 together with the shadow 3 as shown in FIG. 2. As a result, there is a defect that the ampoule A which is not the inferior one as to which there is no shadow 3 except the shadow 4 is removed in the conventional detecting method. Since an amount of such ampoules A reaches about 5 to 15% of the whole amount of the good ampoules, this results in an economic loss which is the defect of the conventional detecting method.

SUMMARY OF THE INVENTION

It is an object of the present invention to provide an accurate and efficient detecting method which may eliminate the defects inherent in the above conventional detecting method and may distinguish the inferior container having in its inner surface a stain such as the scorch and the like from a good container having a harmless flaw.

According to the present invention, the above object is accomplished by a detecting method characterized in that: light beams are projected in at least two different directions upon a side of a test container rotatably driven, one of which light beams penetrates through the container to becomes a transmitted beam, the other of which light beams is reflected from the container to become a reflected beam; both of the transmitted beam and the reflected beam are simultaneously received by a common photo-receptive surface to project shadows thereupon which shadows enable the detecting method of the present invention to detect the inferior container having the stains in its inner surface. Namely, although the harmless flaws and the like produced in manufacturing process of the container are projected as the shadows upon the photo-receptive surface together with the shadows of the stains by means of the transmitted beam as mentioned above, the reflected beam from the harmless flaws and the like eliminates the shadows of the samjes when the reflected beam is received by the common photo-receptive surface together with the above transmitted beam to produce a composite image, because the harmless flaws and the like wave a large reflection factor to produce numerous reflected beams. As a result, the container having the harmless flaws and the like is not detected as the inferior one in the detecting method of the present invention. In the above method, the transmitted beam may be any one of a diffused beam from the diffusion plate, a parallel beam from a beam projecting lens, or a reflected beam from a reflection plate.

It is another object of the present invention to provide an inferior container detecting apparatus which may eliminate the defect inherent in the conventional detecting apparatus, and may detect automatically, accurately, efficiently and exclusively an inferior container having the stains in its inner surface.

According to the present invention, the above another object is accomplished by a detecting apparatus characterized by comprising: a rotary table for placing a test container thereon; at least two light beam projecting members disposed in different positions with each other in the same plane adjacent to the side of the container placed on the rotary table; a photo-receptive member disposed in a position opposite to one of the beam projecting members and having a common photo-receptive surface which receives simultaneously a transmitted beam and a reflected beam, which transmitted beam is projected from the one of the beam projecting members and penetrates through the container, which reflected beam is projected from the other of the beam projecting members and is reflected from the container; and a photo sensor having a photo-receptive surface for convereting a received quantity of light into an electric signal corresponding thereto. Namely, the beams are simultaneously projected from a plurality of the beam projecting members disposed in different directions with each other, to the side of the test container which is placed on the rotary table and is rotatably driven, one of which beams penetrates through the container to become a transmitted beam, the other of which beams is reflected from the container to become a reflected beam, both of the resultant beams are simultaneously projected upon the common photo-receptive surface whereby, of the shadows produced by the transmitted beam, the shadow produced by the harmless flaw and the like is eliminated by the reflected beam so as to make it possible that an image having remaining shadows exclusively produced by the stains is projected upon the photo-receptive surface of the photo-receptive member. Since this image is converted into an electric signal by means of the photo sensor, such electric signal enables the apparatus to detect automatically, very accurately, and very efficiently the inferior container, i.e., the container having the detected shadow.

In the above apparatus of the present invention, the diffusion plate or the beam projecting lens is interposed between the one of the beam projecting members and the rotary table, or the other of the beam projecting members is the reflection plate.

BRIEF DESCRIPTION OF THE DRAWINGS

FIG. 7 is a diagram showing the electric signal converted from the image shown in FIG. 2, by means of the photo sensor;

FIG. 8 is a view showing the image formed on the photo-receptive member, exclusively by means of the reflected beam in each of the above embodiments as to the ampoule forming the image shown in FIG. 2;

FIG. 9 is a diagram showing the electric signal converted from the image shown in FIG. 8, by means of the photo sensor;

FIG. 10 is a view similar to FIG. 2, but shows shadow 4 of FIG. 2 being cancelled;

FIG. 11 is a view showing the electric signal converted by the photo sensor from the image shown in FIG. 10.

DESCRIPTION OF THE PREFERRED EMBODIMENTS

Figure 4:
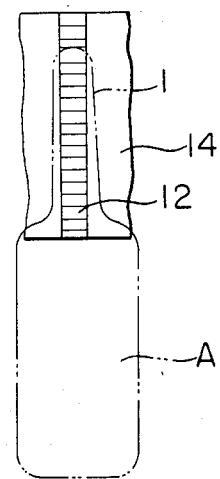
FIG. 4 is a view showing the relative positional relationship between the photo sensor of the first embodiment and the ampoule.
Figure 3:
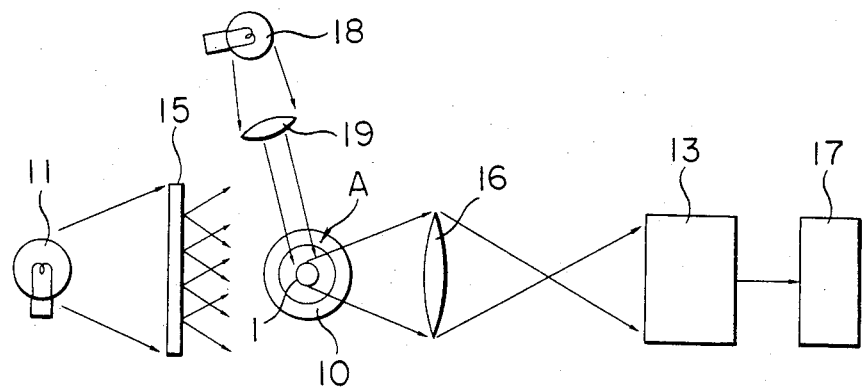
FIG. 3 is a plan view showing an outline of the inspection arrangement according to the one embodiment of the detecting apparatus of the present invention.
Figure 5:
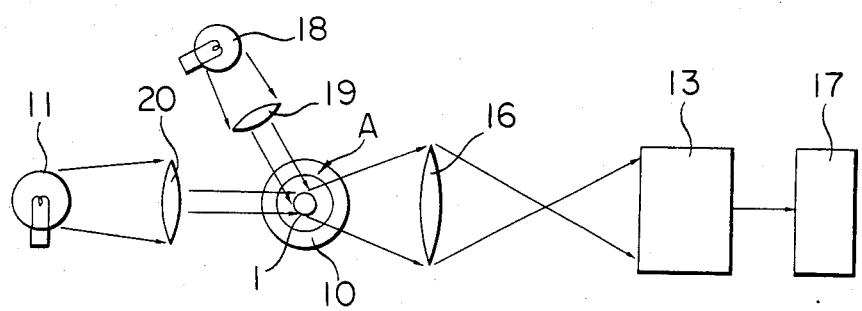
FIG. 5 is a plan view of an outline of the inspection arrangement according to the second embodiment of the detecting apparatus of the present invention.
Figure 6:
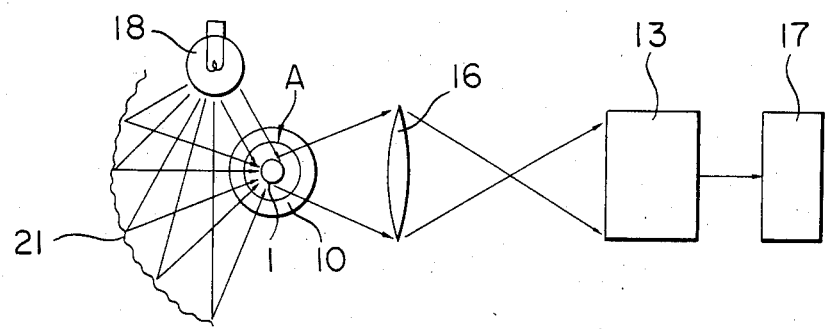
FIG. 6 is a plan view of an outline of the inspection arrangement according to the third embodiment of the detecting apparatus of the present invention.

In the embodiment of the present invention shown in FIG. 3, the numeral 10 designates a rotary table, on which a test ampoule A is placed, which table 10 is rotatably driven by a driving unit (not shown), on a side of which table 10 is disposed a first lamp 11, in a direction opposite to the side of which table 10 is disposed a photo-receptive member 13 on an extension of a straight line passing through the lamp 11 and the rotary table 10. As shown in FIG. 4, on this photo-receptive member 13 is provided a photo sensor 14 having a photo-receptive surface 12 divided longitudinally into a plurality of segments, which sensor 14 converts a quantity of light of an image projected upon the photo-receptive surface 12 into an electric signal. The numeral 15 designates a diffusion plate interposed between the rotary table 10 and the lamp 11, which plate 15 is constructed of a frosted glass and the like and diffuses a beam incident thereon from the lamp 11 so as to project the resultant diffused beam upon the ampoule A. The numeral 16 designates a focusing lens interposed between the rotary table 10 and the photo-receptive member 13; and 17 designates a processing circuit which receives the electric signal to indicate whether the ampoule A is good or not, and feeds to a inferior container discharging unit an energy for actuating the same.

The numeral 18 designates a second lamp disposed at a position different from that of the lamp 11 in substantially same plane. A lens 19 is interposed between the second lamp 18 and the rotary table 10.

Hereinbelow, inspection operation performed in the first embodiment of the present invention will be described: First, the test ampoule A is placed on the rotary table 10, and then the light beams are projected upon the ampoule A from both of the lamps 11 and 18 through the diffusion plate 15 and the lens 19 respectively, while the rotary table 10 is rotatably driven.

Figure 1A:
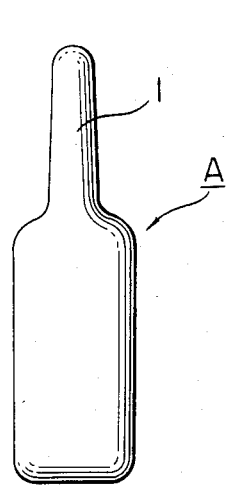
FIG. 1A is a front view of the ampoule as a typical example of the test container to be inspected according to the present invention.
Figure 1B:
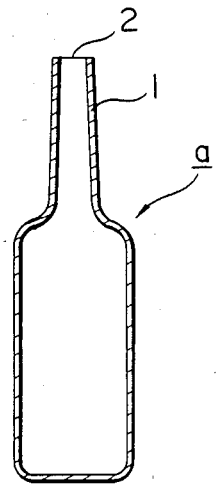
FIG. 1B is a longitudinal sectional front view of a blank of the ampoule shown in FIG. 1A.
Figure 2:
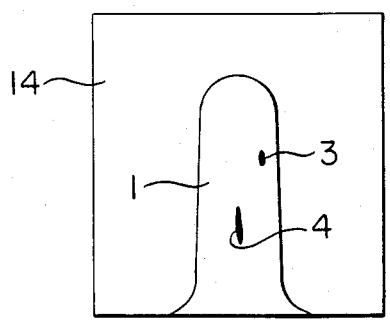
FIG. 2 is a view showing the image of the container detected as the inferior one of the above example on the photo-receptive member of the inferior container detecting apparatus proposed prior to the present invention.

The beam projected from the first lamp 11 penetrates through the ampoule A after being diffused by the diffusion plate 15 and being projected upon the ampoule A substantially uniformly, to become a transmitted beam which is projected upon the photo-receptive surface 12 of the photo sensor of the photo-receptive member 13 through the lens 16 to produce the image of the ampoule A on the photo-receptive surface 12. If only the transmitted beam is projected upon the photo-receptive surface 12 of the photo sensor 14, the image formed on the photo-receptive surface 12 becomes an image similar to that shown in FIG. 2 in which image the shadow 4 of the harmless flaw is also shown together with the shadow 3 of the stain, which image is converted into the electric signal the diagram of which is shown in FIG. 7, in which electric signal an illuminous intensity of a portion corresponding to no flaw and no stain appears as a level 0 while a portion corresponding to the shadows 3, 4 appears as minus signals 23, 24.

On the other hand, a light beam projected from the second lamp 18 is reflected from the ampoule A to become a reflected beam which is projected upon the photo-receptive surface 12 of the photo sensor 14 through the lens 16 together with the transmitted beam to produce the image of the ampoule A. If only the reflected beam is projected upon the photo-receptive surface 12 of the photo sensor 14, a quantity of the light reflected from the harmless flaw and the like of the ampoule A is larger than that reflected from other portion of the ampoule A whereby the harmless flaw and the like are projected as a bright image 4' in contrast with the other portion of the ampoule A projected as a dark image as shown in FIG. 8, which images are converted into electric signals by the photo sensor 14, as shown in FIG. 9. In these electric signals, the other portion having no flaw and the like appears as a level 0 while the portion corresponding to the bright image 4' appears as a plus signal 24'.

Since the transmitted beam and the reflected beam are simultaneously projected upon the photo-receptive member 13 as mentioned above not separately, the images shown in FIGS. 2 and 8 overlap with each other on the photo sensor 14 whereby the shadow 4 is eliminated by the bright image 4'. As a result, only the image as shown in FIG. 10 is projected upon the photo-receptive surface 12 of the photo sensor 14, which image is converted into the electric signal shown in FIG. 11, by means of the photo sensor 14, in which electric signal it is clearly shown that the signals 24, 24' are eliminated with each other and that there is no signal opposite to the signal 23. As for such signal 23, when a standard level "s" is predetermined in the photo sensor 14 which level "s" enables the apparatus to detect the inferior container, the ampoule A producing the signal 23 having a level over the standard level "s" may be distinguished as the inferior container from other good containers.

Since a processing circuit 17 receiving such a signal is provided in this embodiment of the present invention, it is possible to indicate and/or to remove the inferior container by actuating an indicator and/or an inferior container discharging unit (both not shown), respectively by means of the processing circuit 17 when the circuit 17 receives the signal showing the inferior container.

In this embodiment, since the diffusion plate 15 is employed, there is an effect that the ampoule A stands out in bold relief in white shining manner, which diffusion plate 15 may be constructed of a suitable material having such effect other than the frosted glass mentioned above.

Incidentally, since the reflected beam is lower in luminous intensity than the transmitted beam straightly projected, it is necessary to adjust a balance of the luminous intensity between the transmitted beam and the reflected beam.

Since the second and the third embodiments of the present invention are substantially similar to the first embodiment of the present invention, like parts are designated with like reference numerals and character as is in the first embodiment, and parts different from those of the first embodiment will be hereinbelow mainly described:

In the second embodiment, a lens 20 is employed in place of the diffusion plate 15 of the first embodiment, which lens 20 projects a parallel beam on to the ampoule A. In the third embodiment, the lamp 11 employed in the first and the second embodiments is removed, and a reflection plate 21 is employed in place of the diffusion plate 15, which reflection plate 21 has the same effect as that of the diffusion plate 15.

Although particular embodiments of the present invention have been disclosed in detail for illustrative purpose, it will be recognized that variations or modifications of the disclosed method and apparatus, including the rearrangement of the parts, lie within the scope of the present invention.

What is claimed is:

1. A method for detecting a substantially non-reflective flaw in a container which is at least semi-transparent, said container being susceptible to substantially non-reflective flaws which inhibit light transmission therethrough producing shadows and substantially reflective flaws which inhibit light transmission therethrough producing shadows, said method comprising the steps of:
    providing a rotary turntable;
    mounting a container to be tested for non-reflective flaws upon said turntable;
    rotating said turntable, and hence said container;
    providing a first light beam projector;
    projecting a first light beam from said first light beam projector in a first direction so as to pass through said rotating container and thereby form a transmitted light beam;
    providing a photo-receptive surface means for the detection of shadows;
    providing a second light beam projector;
    projecting a second light beam from said second light beam projector in a second direction so as to reflect off of said rotating container and thereby form a reflected light beam;
    simultaneously superposing said transmitted light beam and said reflected light beam on said photo-receptive surface means, whereby said transmitted light beam and said reflected light beam cooperate to form a shadow only for said non-reflective flaws;
    detecting whether a shadow is formed and rejecting any container for which a shadow is formed.

2. The method according to claim 1, wherein said first light beam projector comprises a diffusion plate for the production of a diffused light beam.

3. The method according to claim 1, wherein said first light beam projector comprises a projecting lens for the production of a parallel light beam.

4. The method according to claim 1, wherein said first light beam projector comprises a reflection plate for the production of a first reflected beam.

5. An apparatus for detecting a substantially non-reflective flaw in a container which is at least semi-transparent, said container being susceptible to substantially non-reflective flaws which inhibit light transmission therethrough producing shadows and substantially reflective flaws which inhibit light transmission therethrough producing shadows, said apparatus comprising:
    rotary table means for holding and rotating a container to be tested for non-reflective flaws;
    first light beam projection means for projecting a first light beam in a first direction so as to pass through said container held in said rotary table means as it rotates and thereby form a transmitted light beam;
    second light beam projection means for projecting a second light beam in a second direction so as to reflect off of said container held in said rotary table means as it rotates and thereby form a reflected light beam;
    photo-receptive surface means, disposed opposite said first light beam projection means relative to said rotary table means in said first direction, for receiving said transmitted light beam and said reflected light beam and for detecting shadows therein, said first and second directions being related so as to produce superposition of said transmitted light beam and said reflected light beam on said photo-receptive surface means;

processing circuit means, operably connected to said photo-receptive surface means, for producing a signal upon upon detection of a shadow.

6. The apparatus according to claim 5, wherein said first light beam projector comprises a diffusion plate for the production of a diffused light beam.

7. The apparatus according to claim 5, wherein said first light beam projector comprises a projecting lens for the production of a parallel light beam.

8. The apparatus according to claim 5, wherein said first light beam projector comprises a reflection plate for the production of a first reflected beam.

* * * * *